US011998630B2

(12) United States Patent
Abe

(10) Patent No.: US 11,998,630 B2
(45) Date of Patent: Jun. 4, 2024

(54) RESIN BEADS, METHOD FOR PRODUCING RESIN BEADS AND PRODUCT USING RESIN BEADS

(71) Applicant: DAINICHISEIKA COLOR & CHEMICALS MFG. CO., LTD., Tokyo (JP)

(72) Inventor: Takashi Abe, Tokyo (JP)

(73) Assignee: Dainichiseika Color & Chemicals Mfg. Co., Ltd., Tokyo (JP)

( * ) Notice: Subject to any disclaimer, the term of this patent is extended or adjusted under 35 U.S.C. 154(b) by 0 days.

(21) Appl. No.: 17/905,233

(22) PCT Filed: Feb. 25, 2021

(86) PCT No.: PCT/JP2021/007183
§ 371 (c)(1),
(2) Date: Aug. 29, 2022

(87) PCT Pub. No.: WO2021/177141
PCT Pub. Date: Sep. 10, 2021

(65) Prior Publication Data
US 2023/0136180 A1 May 4, 2023

(30) Foreign Application Priority Data
Mar. 4, 2020 (JP) .................................. 2020-036983

(51) Int. Cl.
| A61K 8/73 | (2006.01) |
| A61K 8/02 | (2006.01) |
| A61Q 1/02 | (2006.01) |
| A61Q 1/12 | (2006.01) |
| A61Q 17/04 | (2006.01) |
| A61Q 19/00 | (2006.01) |

(52) U.S. Cl.
CPC .............. *A61K 8/731* (2013.01); *A61K 8/025* (2013.01); *A61Q 1/02* (2013.01); *A61Q 19/00* (2013.01)

(58) Field of Classification Search
None
See application file for complete search history.

(56) References Cited

U.S. PATENT DOCUMENTS

| 4,663,447 A | 5/1987 | Yamazaki et al. |
| 4,968,350 A | 11/1990 | Bindschaedler et al. |
| 5,244,734 A | 9/1993 | Okuma et al. |
| 5,245,024 A | 9/1993 | Scarpa et al. |
| 5,972,507 A | 10/1999 | Morimoto et al. |
| 6,225,461 B1 | 5/2001 | Akimoto et al. |
| 6,541,627 B1 | 4/2003 | Ono et al. |
| 6,571,802 B1 | 6/2003 | Yamashita |
| 8,192,748 B2 | 6/2012 | Kuroda |
| 11,548,999 B2 | 1/2023 | Abe |
| 11,628,134 B2 * | 4/2023 | Kobayashi ............. A61K 8/817 424/401 |
| 2003/0012941 A1 | 1/2003 | Fujita et al. |
| 2005/0118121 A1 | 6/2005 | Kuroda |
| 2005/0203278 A1 | 9/2005 | McCreight et al. |
| 2008/0131597 A1 | 6/2008 | Takehara et al. |
| 2009/0044942 A1 | 2/2009 | Gupta |
| 2009/0280186 A1 | 11/2009 | Yaginuma et al. |
| 2010/0087552 A1 | 4/2010 | Shiomi et al. |
| 2010/0178332 A1 | 7/2010 | Kakizawa et al. |
| 2011/0282049 A1 | 11/2011 | Shelton et al. |
| 2016/0303032 A1 | 10/2016 | Kamei |
| 2020/0179261 A1 * | 6/2020 | Kobayashi ............... A61K 8/36 |
| 2020/0299488 A1 | 9/2020 | Kobayashi et al. |
| 2022/0025131 A1 | 1/2022 | Shibata et al. |
| 2022/0267573 A1 | 8/2022 | Abe |

(Continued)

FOREIGN PATENT DOCUMENTS

| CN | 102911379 | 2/2013 |
| EP | 0309527 | 1/1993 |

(Continued)

OTHER PUBLICATIONS

Of El-Habashy et al., Int. J. Nanomed., 2016, vol. 11 pp. 2369-2380. (Year: 2016).*
Scarfato et al., J. App. Poly. Sci., 2008, vol. 109, pp. 2994-3001. (Year: 2008).*
International Search Report, issued in the corresponding PCT application No. PCT/JP2021/007183, dated May 18, 2021, 5 pages (including machine translation).
"Measuring method for specific gravity of solid", JIS Handbook 31 Chemical analysis, pp. 751-755, Japanese Standards Association, Apr. 20, 1997, cited in the Notice of Reasons for Revocation (A concise explanation of relevance provided in Notice of Reasons for Revocation for JP patent application 2020-036983, dated Aug. 20, 2021).

(Continued)

*Primary Examiner* — Brian Gulledge
(74) *Attorney, Agent, or Firm* — HSML P.C.

(57) ABSTRACT

The present invention provides resin beads that can provide various types of products such as cosmetics which are unlikely to generate an odor and have superior tactile impression and spreadability on the skin and that can be substituted for resin particles composed of a synthetic material derived from petroleum, and the present invention also provides various types of products such as cosmetics using the resin beads. The resin beads are formed with a resin containing a cellulose derivative as a main component. In the resin beads, the cellulose derivative is at least one selected from the group consisting of cellulose acetate, cellulose acetate propionate, ethyl cellulose, and hydroxypropyl methyl cellulose, the volume average particle diameter is 50 μm or smaller, the degree of sphericity is 0.7 to 1.0, the degree of surface smoothness is 80 to 100%, the acetyl group content ratio is 15% by mass or less, and the propionyl group content ratio is 10% by mass or more. In addition, the present invention provides a product of any one of a cosmetic, a dermatological preparation, a paint, a shaped article, a film, a coating agent, and a resin composition, which contain the resin beads.

18 Claims, 1 Drawing Sheet

(56) References Cited

U.S. PATENT DOCUMENTS

| | | | |
|---|---|---|---|
| 2022/0275163 A1 | 9/2022 | Shibata et al. | |
| 2023/0303782 A1 | 9/2023 | Abe | |

FOREIGN PATENT DOCUMENTS

| | | |
|---|---|---|
| EP | 0750007 | 12/1996 |
| EP | 3613794 | 2/2020 |
| EP | 3943530 | 1/2022 |
| EP | 3998300 | 5/2022 |
| EP | 4116357 | 1/2023 |
| EP | 4209514 | 7/2023 |
| EP | 4234043 | 8/2023 |
| JP | 49-019183 | 2/1974 |
| JP | 50-041954 | 4/1975 |
| JP | 51-090352 | 8/1976 |
| JP | S55-028763 | 2/1980 |
| JP | 59-219333 | 12/1984 |
| JP | 60-155245 | 8/1985 |
| JP | 62-253601 | 11/1987 |
| JP | 63-068645 | 3/1988 |
| JP | 63-095237 | 4/1988 |
| JP | 06-254373 | 9/1994 |
| JP | 11-181147 | 7/1999 |
| JP | 2931810 | 8/1999 |
| JP | H11-279201 | 10/1999 |
| JP | 2000-309503 | 11/2000 |
| JP | 2000-309508 | 11/2000 |
| JP | 2002-205917 | 7/2002 |
| JP | 2002-363445 | 12/2002 |
| JP | 2003-146829 | 5/2003 |
| JP | 2003-252903 | 9/2003 |
| JP | 2005-264120 | 9/2005 |
| JP | 2006-131875 | 5/2006 |
| JP | 2006523752 | 10/2006 |
| JP | 2006-328245 | 12/2006 |
| JP | 2007-528436 | 10/2007 |
| JP | 4076955 | 4/2008 |
| JP | 2010-155982 | 7/2010 |
| JP | 2012-092191 | 5/2012 |
| JP | 2013-221000 | 10/2013 |
| JP | 2014-224183 | 12/2014 |
| JP | 2015-117190 | 6/2015 |
| JP | 2017-052961 | 3/2017 |
| JP | 2018-008392 | 1/2018 |
| JP | 2018-052909 | 4/2018 |
| JP | 2018-127579 | 8/2018 |
| JP | 2019-031631 | 2/2019 |
| JP | S609726 | 11/2019 |
| JP | 2020-075878 | 5/2020 |
| JP | 6694559 | 5/2020 |
| JP | 2020-132616 | 8/2020 |
| JP | 2020-152851 | 9/2020 |
| WO | 88/08011 | 10/1988 |
| WO | 1999/028350 | 6/1999 |
| WO | 2003/075863 | 9/2003 |
| WO | 2004083253 | 9/2004 |
| WO | WO-2004083253 A1 * | 9/2004 ............ C08B 13/00 |
| WO | 2009/123148 | 10/2009 |
| WO | 2015/029790 | 3/2015 |
| WO | 2016/013568 | 1/2016 |
| WO | 2019/156116 | 8/2019 |
| WO | WO-2019156116 A1 * | 8/2019 .......... A61K 8/0241 |
| WO | 2020/188698 | 9/2020 |

OTHER PUBLICATIONS

Technical Data Sheet, "Cellulose Acetate Propionate CAP-482-0.5", Eastman, cited in the Notice of Reasons for Revocation (dated Mar. 30, 2022), 4 pages, 2021.

Notice of Reasons for Revocation of JP patent 6779400 (JP patent application 2020-036983), issued in the Trial/Appeal Opposition No. JP 2021-700373, dated Aug. 20, 2021, 41 pages (including machine translation).

Notice of Reasons for Revocation of JP patent 6779400 (JP patent application 2020-036983) with allowance of amendments, issued in the Trial/Appeal Opposition No. JP 2021-700373, dated Mar. 30, 2022, 57 pages (including machine translation).

International Search Report, issued in the related PCT application No. PCT/JP2020/026551, dated Sep. 24, 2020, 7 pages (including translation).

Extended European Search Report, issued in the related European Patent Application No. 20837372.0, dated Jul. 29, 2022, 10 pages.

"Novel colored complex cellulose beads", Society of Cosmetic Scientists, 2003, 1 page.

Brazilian Office Action, issued in the related Brazilian Patent Application No. 112022000453-2, dated Jun. 10, 2022, 8 pages.

International Search Report, issued in the related PCT application No. PCT/JP2021/034810, dated Nov. 30, 2021, 5 pages (including translation).

Extended European Search Report, issued in the corresponding European Patent Application No. 21864062.1, dated Oct. 13, 2023, 9 pages.

Extended European Search Report, issued in the corresponding European Patent Application No. 21764155.4, dated Oct. 13, 2023, 8 pages.

Takashi Abe, U.S. Appl. No. 18/257,531, filed Jun. 14, 2023, titled "Resin Beads, Method for Producing Resin Beads, and Product Using Resin Beads", 48 pages.

International Search Report, issued in the corresponding PCT application No. PCT/JP2021/029501, dated Sep. 21, 2021, 7 pages (including machine translation).

Extended European Search Report, issued in the related European patent application No. 21909837.3, dated Mar. 27, 2024, 8 pages.

"Plastic Additives", Sakai Chemical Industry Co., Ltd., (2016) downloaded Apr. 2024, 4 pages, available at https://www.sakai-chem.co.jp/en/products_services_plastic_additive.php.

US Non-Final Office Action, issued in the U.S. Appl. No. 18/257,531, dated Apr. 8, 2024, 28 pages.

* cited by examiner

[Figure 1]
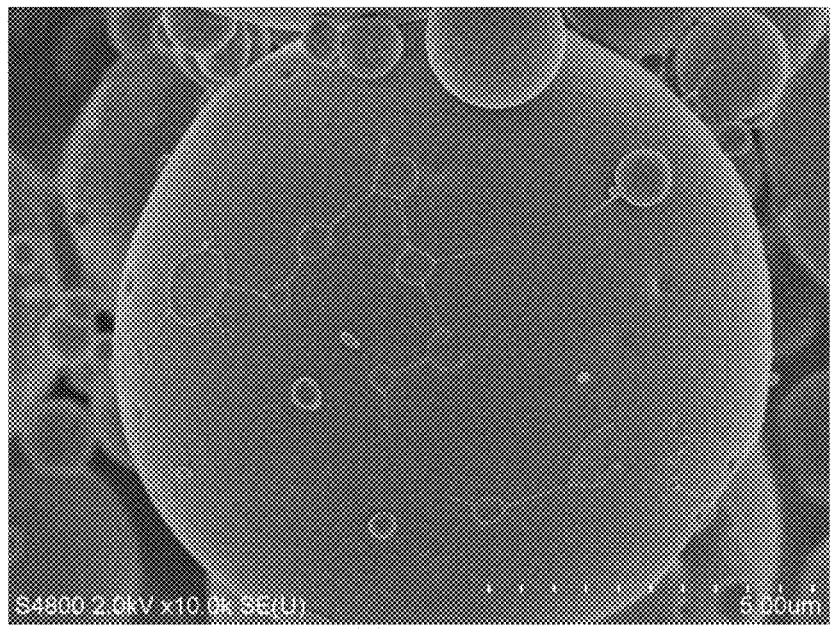
[Figure 2]
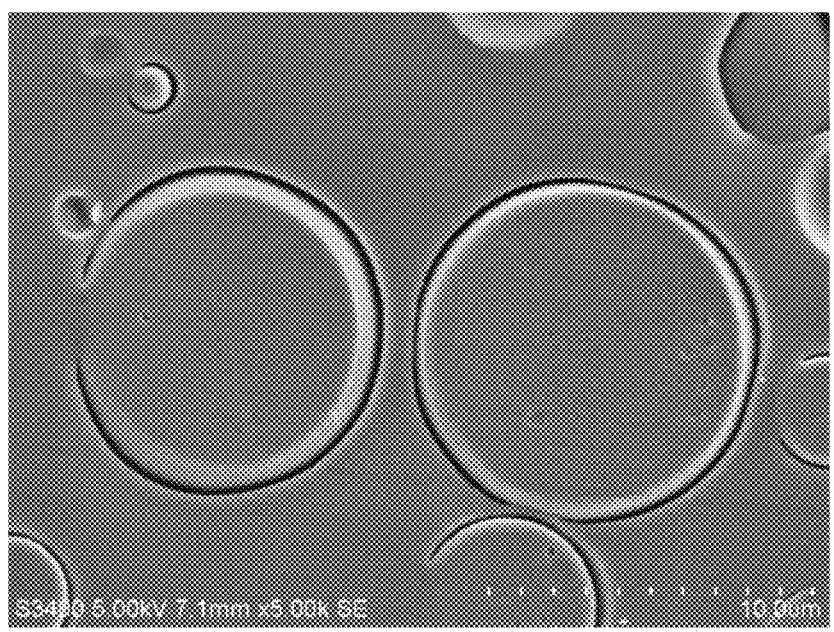

RESIN BEADS, METHOD FOR PRODUCING RESIN BEADS AND PRODUCT USING RESIN BEADS

TECHNICAL FIELD

The present invention relates to resin beads containing a cellulose derivative as a main component, a method for producing the resin beads, and products, such as cosmetics, obtained using the resin beads.

BACKGROUND ART

In the past, resin beads have been used in various fields, such as a matting agent, a slipping agent, and an antiblocking agent, from the properties derived from the spherical shape. Further, various resin powders (resin particles), such as resin beads, have been used in order to improve the properties, such as spreadability, of cosmetics for makeup. However, materials for forming resin beads to be blended in cosmetics have been being changed from synthetic materials derived from petroleum to natural materials due to the problems and the like, such as marine pollution caused by microplastics, in recent years.

For example, powdery cellulose useful as a scrubbing agent has been proposed as spherical resin particles composed of a natural material (Patent Literature 1). Further, cellulose derivative fine particles (Patent Literature 2) which are used for a diagnostic drug and a spherical cellulose powder (Patent Literature 3) which is used for cosmetics have been proposed. Furthermore, porous cellulose particles (Patent Literatures 4 and 5) which are used as a filler for chromatography, biodegradable cellulose acetate particles (Patent Literature 6) having a high degree of sphericity, and the like have been proposed.

CITATION LIST

Patent Literature

Patent Literature 1: Japanese Patent Laid-Open No. 2018-052909
Patent Literature 2: International Publication No. WO 2009/123148
Patent Literature 3: Japanese Patent Laid-Open No. 2013-221000
Patent Literature 4: International Publication No. WO 2016/013568
Patent Literature 5: International Publication No. WO 2015/029790
Patent Literature 6: Japanese Patent No. 6609726

SUMMARY OF INVENTION

Technical Problem

However, the powdery cellulose and the like proposed in Patent Literatures 1, 2, 4, and 5 do not have a suitable particle diameter as a material to be blended in cosmetics for makeup or skin care. In addition, copper ammonia needs to be used when the cellulose derivative fine particles proposed in Patent Literature 2 are produced, and therefore the cellulose derivative fine particles cannot necessarily be said to be suitable as a material for cosmetics in which heavy metals are desired to be reduced as much as possible.

Further, the spherical cellulose powder and the like proposed in Patent Literatures 3 to 6 have a low degree of sphericity, and the particle surface thereof is not so smooth. For this reason, the spreadability on the skin cannot be said to be satisfactory so much when the spherical cellulose powders and the like are blended in cosmetics, so that rough surfaces have been likely to be felt. In addition, light scattering is likely to occur due to the roughness of the particle surfaces and the non-solid structure, and therefore the feel of the cosmetics has been likely to change significantly accompanying wetting of the powder and use of the powder in a solution.

Furthermore, porous cellulose particles and the like proposed in Patent Literatures 4 and 5 are likely to adsorb moisture because they are porous. For this reason, when the porous cellulose particles and the like are blended in cosmetics, the cosmetics themselves are likely to be made unstable, and therefore the porous cellulose particles and the like cannot necessarily be said to be suitable as a material for cosmetics.

Moreover, the cellulose acetate particles proposed in Patent Literature 6 give dry tactile impression, and therefore when the cellulose acetate particles are used as a tactile impression improver, the cellulose acetate particles cannot necessarily be said to be suitable for a material that gives "moist tactile impression," which is required in the market. In addition, the cellulose acetate particles are likely to undergo hydrolysis with time, and acetic acid generated by the hydrolysis releases an offensive smell, and therefore the cellulose acetate particles cannot necessarily be said to be suitable as a material for cosmetics.

The present invention has been completed in view of the problems of such conventional techniques, and an object of the present invention is to provide resin beads that can provide various types of products such as cosmetics which are unlikely to generate an odor and have superior tactile impression and spreadability on the skin and that can be substituted for resin particles composed of a synthetic material derived from petroleum, and to provide various types of products such as cosmetics using the resin beads. Another object of the present invention is to provide a method for producing resin beads that can provide various types of products such as cosmetics which are unlikely to generate an odor and have superior tactile impression and spreadability on the skin and that can be substituted for resin particles composed of a synthetic material derived from petroleum.

Solution to Problem

That is, according to the present invention, resin beads, described below, are provided.

[1] Resin beads formed with a resin comprising a cellulose derivative as a main component, wherein the cellulose derivative is at least one selected from the group consisting of cellulose acetate, cellulose acetate propionate, ethyl cellulose, and hydroxypropyl methyl cellulose, the resin beads have a volume average particle diameter of 50 μm or smaller, a degree of sphericity of 0.7 to 1.0, a degree of surface smoothness of 80 to 100%, an acetyl group content ratio of 15% by mass or less, and a propionyl group content ratio of 10% by mass or more.

[2] The resin beads according to [1], wherein the cellulose derivative is cellulose acetate propionate.

[3] The resin beads according to [1] or [2], having a degree of solidity of 70 to 100% by volume.

[4] The resin beads according to any one of [1] to [3], wherein the resin beads comprise at least any one of a pigment and a dye.

[5] The resin beads according to any one of [1] to [4], wherein the resin beads comprise: a pigment; and at least any one of a surfactant, a dispersant, and a polymer dispersant.

[6] The resin beads according to [4] or [5], wherein the pigment is a treated pigment treated with at least one selected from the group consisting of a silicone, a fatty acid, a metal salt of a fatty acid, an amino acid, and a metal salt of an amino acid.

[7] The resin beads according to any one of [1] to [6], wherein the resin beads comprise at least any one of an ultraviolet absorbing agent and an ultraviolet scattering agent.

[8] The resin beads according to any one of [1] to [7], wherein the resin beads are treated beads treated with at least one selected from the group consisting of a silicone, a fatty acid, a metal salt of a fatty acid, an amino acid, and a metal salt of an amino acid.

In addition, according to the present invention, a method for producing resin beads, described below, is provided.

[9] A method for producing resin beads, being a method for producing the resin beads according to any one of [1] to [8], the method comprising: a step of mixing an oil phase comprising the cellulose derivative and an organic solvent that dissolves the cellulose derivative and has a solubility to 100 g of water at 25° C. of 0.1 to 50.0 g with an aqueous phase comprising a dispersion stabilizer, thereby preparing a suspension comprising oil droplets comprising the cellulose derivative and the organic solvent; and a step of adding water to the suspension, thereby contracting the oil droplets.

[10] The method for producing resin beads according to [9], wherein the water is added to the suspension over 30 minutes or longer.

[11] The method for producing resin beads according to [9] or [10], wherein a liquid amount of the water to be added to the suspension is 0.5 times or more based on a liquid amount of the suspension on a mass basis.

[12] The method for producing resin beads according to any one of [9] to [11], wherein the aqueous phase further comprises a second organic solvent.

[13] The method for producing resin beads according to any one of [9] to [12], wherein a liquid amount of the aqueous phase is 3.0 times or less based on a liquid amount of the oil phase on a mass basis.

[14] The method for producing resin beads according to any one of [9] to [13], wherein the organic solvent is at least one selected from the group consisting of a ketone-based solvent, an ester-based solvent, an alcohol, a glycol, an ether-based solvent, a halogenated alkyl, and a nitrated alkyl.

[15] The method for producing resin beads according to any one of [9] to [14], wherein a liquid amount of the organic solvent is 2.0 times or more based on an amount of the cellulose derivative on a mass basis.

[16] The method for producing resin beads according to any one of [9] to [15], wherein the dispersion stabilizer is a water-soluble polymer.

[17] The method for producing resin beads according to any one of [9] to [16], wherein a content of the dispersion stabilizer in the aqueous phase is 30% by mass or less.

Further, according to the present invention, a product, described below, is provided.

[18] A product of any one of a cosmetic, a dermatological preparation, a paint, a shaped article, a film, a coating agent, and a resin composition, the product comprising resin beads, wherein the resin beads are the resin beads according to any one of [1] to [8].

Advantageous Effects of Invention

The present invention can provide: resin beads that can provide various types of products such as cosmetics which are unlikely to generate an odor and have superior tactile impression and spreadability on the skin and that can be substituted for resin particles composed of a synthetic material derived from petroleum; and various types of products such as cosmetics using the resin beads. Further, the present invention can provide a method for producing resin beads that can provide various types of products such as cosmetics which are unlikely to generate an odor and have superior tactile impression and spreadability on the skin and that can be substituted for resin particles composed of a synthetic material derived from petroleum.

BRIEF DESCRIPTION OF DRAWINGS

FIG. 1 is an electron micrograph showing a state of surfaces of resin beads produced in Example 1.

FIG. 2 is an electron micrograph showing states of sections of resin beads produced in Example 1.

DESCRIPTION OF EMBODIMENTS

Hereinafter, embodiments of the present invention will be described, but the present invention is not limited to the following embodiments. Note that various physical property values in the present specification are values at normal temperature (25° C.) unless otherwise noted.

The present inventors have conducted various studies on resin beads that can provide various types of products such as cosmetics imparted with superior tactile impression, spreadability on the skin, transparency, and product stability and that are composed of a natural material, and on the method for producing the resin beads. As a result, the present inventors have found that by adopting the constitution described below, resin beads that are substantially formed with a natural material and that can provide various types of products such as cosmetics imparted with the above-described various properties can be obtained. That is, the resin beads of the present invention are resin beads formed with a resin containing a cellulose derivative as a main component. The resin beads of the present invention have a volume average particle diameter of 50 μm or smaller, a degree of sphericity of 0.7 to 1.0, a degree of surface smoothness of 80 to 100%, and an acetyl group content ratio of 25% by mass or less, and a propionyl group content ratio of 10% by mass or more.

The volume average particle diameter of the resin beads is 50 μm or smaller, preferably 0.5 to 40 μm, and more preferably 1 to 30 μm. By setting the volume average particle diameter to the above-described range, the slipperiness and soft-focus performance, which are required in resin beads to be blended in cosmetics or the like, can effectively be exhibited.

The degree of sphericity of the resin beads is 0.7 or more and 1.0 or less, preferably 0.75 to 1.0 or less, more preferably 0.8 to 1.0 or less, and particularly preferably 0.85 to 0.99 or less. By setting the degree of sphericity to the above-described range, favorable tactile impression and spreadability on the skin, which are required in resin beads to be blended in cosmetics or the like, can effectively be exhibited.

The degree of sphericity, which is an index of whether the resin beads have a perfectly spherical shape or not, can be measured and calculated according to the procedure described below. Firstly, a SEM image of the resin beads, taken with a scanning electron microscope (SEM), is subjected to image analysis to calculate the degree of circularity C for each resin bead from the following formula (1). Subsequently, the arithmetic average value of the degrees of circularity C for 100 or more resin beads arbitrarily selected is defined as the degree of sphericity.

$$C=(4\pi S_1)/(L^2) \quad (1)$$

In the formula (1), $S_1$ represents the area (projected area) of each resin bead in the image, and L represents the length of the outer peripheral part of the resin bead in the image. As the value of the degree of circularity C is closer to 1, each of the shapes of the particles is closer to a perfect sphere.

The degree of surface smoothness of the resin beads is 80 to 100%, preferably 85% to 100%, and more preferably 90 to 99%. By setting the degree of surface smoothness to the above-described range, favorable tactile impression and spreadability on the skin, which are required in resin beads to be blended in cosmetics or the like, can effectively be exhibited.

The degree of surface smoothness of the resin beads can be measured according to the procedure described below. That is, a SEM image (×5,000) of the resin beads, taken with a scanning electron microscope (SEM), is observed to calculate the degree of smoothness M for each resin bead from the following formula (2). Subsequently, the arithmetic average value of the degrees of smoothness M for 100 or more resin beads arbitrarily selected is defined as the degree of surface smoothness. As the value of the degree of smoothness M is closer to 1, the surfaces of the particles are closer to be smooth.

$$M=(1-(S_3)/(S_2))\times 100 \quad (2)$$

In the formula (2), $S_2$ represents the area (projected area) of each resin bead in the image, and in the case where a resin bead and a circle that approximates the resin bead are overlapped, $S_3$ represents, in the regions formed by the contour of the resin bead and the contour of the circle, the sum total of the areas of regions that exist inside the contour of the overlapped circle and the area of regions that exist outside the contour of the overlapped circle.

Among the cellulose derivatives, the cellulose esters may generate a free acid by partial hydrolysis. Therefore, in resin beads formed with a cellulose ester, the odor of the free acid may cause a problem depending on the product for which the resin beads are applied. With regard to the resin beads formed with a resin containing a cellulose derivative as a main component, by controlling (reducing) the acetyl group ($CH_3CO$—) content ratio, the release of acetic acid generated by hydrolysis can be suppressed, so that generation of an odor can be suppressed. Specifically, the acetyl group content ratio in the resin beads of the present invention is 25% by mass or less, preferably 20% by mass or less, more preferably 15% by mass or less, and particularly preferably 10% by mass or less. By setting the acetyl group content ratio to the above-described range, the offensive smell, such as an acetic acid smell, generated with time can be suppressed and resin beads that can suitably be blended in cosmetics or the like can be produced.

The acetyl group content ratio in the resin beads can be adjusted by, for example, using a cellulose derivative having an acetyl group content ratio in a predetermined range as a raw material. As for the cellulose derivative, a commercially available cellulose derivative may be used as served, or a cellulose derivative in which the acetyl group content ratio has been adjusted by hydrolysis or esterification according to a usual method may be used. Further, the acetyl group content ratio may be controlled by mixing a plurality of resin beads having different acetyl group content ratios in such a way that the acetyl group content ratio in the whole resin beads falls within a predetermined range.

The propionyl group ($CH_3CH_2CO$—) content ratio in the resin beads is 10% by mass or more, preferably 15 to 60% by mass, and more preferably 20 to 50% by mass. By setting the propionyl group content ratio to the above-described range, resin beads having "moist tactile impression," which is required in resin beads to be blended in cosmetics or the like can be produced.

The type of substituent in the ester site of a cellulose ester among the cellulose derivatives gives a significant influence on the tactile impression of the resin beads. In addition, it is inferred that the tactile impression of the resin beads is exhibited by the characteristics specific to the substituent in the ester site, and besides, the solubility of the cellulose ester into an organic solvent which is used in the production method described later, the orientation of molecules in a suspension, and the like. Among others, by adequately setting the propionyl group content ratio in the cellulose derivative which is used as a raw material, the "moist tactile impression" can be exhibited.

The propionyl group content ratio in the resin beads can be adjusted by, for example, using a cellulose derivative in which the propionyl group content ratio is in a predetermined range as a raw material. As for the cellulose derivative, a commercially available cellulose derivative may be used as served, or a cellulose derivative in which the propionyl group content ratio has been adjusted by hydrolysis or esterification according to a usual method may be used. Further, the propionyl group content ratio may be controlled by mixing a plurality of resin beads having different propionyl group content ratios in such a way that the propionyl group content ratio in the whole resin beads falls within a predetermined range.

The degree of solidity of the resin beads is preferably 70 to 100% by volume, more preferably 75 to 100% by volume, and particularly preferably 80 to 99% by volume. By setting the degree of solidity within the above-described range, the transparency which is required in the resin beads to be blended in the cosmetics or the like can effectively be exhibited. When the degree of solidity of the resin beads is less than 70% by volume, light scattering occurs due to empty regions, so that the transparency is likely to lower. In addition, when the degree of solidity lowers, the oil absorption changes. For this reason, when resin beads having a low degree of solidity are blended in a product such as a cosmetic, the product stability may be somewhat deteriorated.

The degree of solidity of the resin beads can be measured and calculated according to the procedure described below.

Firstly, a SEM image of sections of the resin beads, taken with a scanning electron microscope (SEM), is subjected to image analysis to calculate the volume of the part filled with the resin for each resin bead. Subsequently, the average value of the volumes of the parts filled with the resin for 20 or more resin beads arbitrarily selected is defined as the degree of solidity (% by volume).

The resin for forming the resin beads of the present invention contains a cellulose derivative as a main component. The resin for forming the resin beads preferably consists of only a cellulose derivative. The cellulose derivative is obtained by modifying cellulose having three hydroxy groups in one unit. The cellulose derivative may be the one obtained by substituting one hydroxy group in cellulose with a particular substituent, the one obtained by substituting two hydroxy groups with a particular substituent, or the one obtained by substituting three hydroxy groups with a particular substituent. The structure of the substituent may be any one of a linear structure, a branched structure, and a cyclic structure. In addition, the cellulose derivative may be a salt. A cellulose derivative appropriately selected from known cellulose derivatives taking the purpose of use of the resin beads into consideration can be used as the cellulose derivative. Among the cellulose derivatives, cellulose esters which are used, as a natural cellulose derivative, for products, such as cosmetics, are preferable.

Specific examples of the cellulose derivative include methyl cellulose, ethyl cellulose, cellulose acetate, cellulose acetate butyrate, cellulose acetate propionate, nitrocellulose, hydroxypropyl methyl cellulose, hydroxyethyl methyl cellulose, hydroxypropyl cellulose, hydroxypropyl methyl cellulose phthalate, hypromellose acetate succinate, carboxymethyl cellulose, and cellulose glycolic acid ether. Note that examples of the cellulose acetate include acetyl cellulose, diacetyl cellulose, and triacetyl cellulose. These cellulose derivatives can be used singly, or two or more of these cellulose derivatives can be used in combination.

Among the cellulose derivatives, specific examples of the cellulose esters include methyl cellulose, ethyl cellulose, acetyl cellulose, diacetyl cellulose, triacetyl cellulose, cellulose acetate butyrate, and cellulose acetate propionate. Among these, cellulose acetate, cellulose acetate propionate, ethyl cellulose, hydroxypropyl methyl cellulose, and the like are preferable.

The resin beads may contain at least any one of a pigment and a dye according to the application. To obtain the resin beads containing a pigment or a dye, the suspension may be prepared using, for example, the oil phase further containing at least any one of the pigment and the dye. Examples of the pigment include metal oxides, such as titanium dioxide, zinc oxide, Bengala, yellow iron oxide, and black iron oxide, and besides, Food Yellow No. 4, Food Red No. 202, and Food Blue No. 1, which are Japanese names of certified colors, and carbon black. In addition, extender pigments, such as mica, talc, kaolin, and calcium carbonate, can also be used. Examples of the dye include Food Red No. 104, Food Yellow No. 5, and Food Blue No. 1.

The resin beads preferably contain: a pigment; and at least any one of a surfactant, a dispersant, and a polymer dispersant. In addition, the pigment is preferably a treated pigment treated with at least one selected from the group consisting of a silicone, a fatty acid, a metal salt of a fatty acid, an amino acid, and a metal salt of an amino acid.

The resin beads may contain at least any one of an ultraviolet absorbing agent and an ultraviolet scattering agent according to the application. To obtain the resin beads containing an ultraviolet absorbing agent or an ultraviolet scattering agent, the suspension may be prepared using, for example, the oil phase further containing at least any one of the ultraviolet absorbing agent and the ultraviolet scattering agent. Examples of the ultraviolet absorbing agent and the like include fine particle titanium dioxide, fine particle zinc oxide, a cinnamic acid-based ultraviolet absorbing agent, and a dibenzoylmethane-based ultraviolet absorbing agent.

The resin beads are preferably treated beads treated with at least one selected from the group consisting of a silicone, a fatty acid, a metal salt of a fatty acid, an amino acid, and a metal salt of an amino acid.

Nest, a method for producing the above-mentioned resin beads will be described. The method for producing resin beads of the present invention is a method for producing the above-mentioned resin beads and includes a step (suspension preparation step) of mixing an oil phase (first liquid) containing the cellulose derivative and an organic solvent that dissolves the cellulose derivative with an aqueous phase (second liquid) containing a dispersion stabilizer, thereby preparing a suspension containing oil droplets containing the cellulose derivative and the organic solvent.

In the suspension preparation step, the oil phase containing a cellulose derivative and an organic solvent that dissolves the cellulose derivative is mixes with an aqueous phase containing a dispersion stabilizer. By mixing and, if necessary, stirring the oil phase and the aqueous phase, a suspension in which oil droplets containing the cellulose derivative and the organic solvent are dispersed in water can be obtained. These oil droplets are present in a dispersed state in water, and therefore the organic solvent in the oil droplets transfers gradually into water. Then, the oil droplets contract accompanying the transfer of the organic solvent, so that the cellulose derivative dissolved in the solvent precipitates gradually. The precipitated cellulose derivative grows while retaining smooth surfaces as shown in FIG. 1. Finally, the precipitated cellulose derivative is fixed, and substantially solid resin beads are formed. Whether the contraction of the oil droplets has occurred or not can be decided by analyzing an image observed using an optical microscope, an electron microscope, or the like. When such contraction of the oil droplets occurs, resin beads which have high sphericity (degree of sphericity), which are substantially solid, which have smooth surfaces, and which have a desired particle diameter can thereby be obtained. Then, by using the resin beads obtained in this way, various types of products such as cosmetics which are unlikely to generate an odor and which have superior tactile impression and spreadability on the skin can be provided.

As the organic solvent (first organic solvent) contained in the oil phase, a known organic solvent which can dissolve the cellulose derivative can be used. As the specific examples of the organic solvent, ester-based solvents, such as methyl formate, ethyl formate, methyl acetate, ethyl acetate, and butyl acetate; ketone-based solvents, such as acetone, methyl ethyl ketone, methyl isobutyl ketone, and cyclohexanone; alcohols, such as ethanol and n-butanol; ether-based solvents, such as ethyl cellosolve, butyl cellosolve, and ethylene glycol diethyl ether; glycol ether-based solvents, such as dipropylene glycol monomethyl ether; glycol ester-based solvents, such as propylene glycol monomethyl ether acetate; chlorine-based solvents, such as methylene chloride, chloroform, and tetrachloroethane; nitromethane; propylene carbonate, and the like can be used. These organic solvents can be used singly, or two or more of these organic solvents can be used in combination.

The organic solvent is preferably a ketone-based solvent, an ester-based solvent, an alcohol, a glycol, an ether-based solvent, a halogenated alkyl, or nitrated alkyl. Among others, the organic solvent is further preferably methyl ethyl ketone, ethyl acetate, butanol, propylene glycol monobutyl ether, propyl acetate, or propylene glycol monomethyl ether acetate.

The organic solvent in the oil droplets contained in the suspension transfers gradually into the aqueous phase. However, when the water-solubility of the organic solvent is too high, the organic solvent is likely to transfer rapidly from the oil droplets into the aqueous phase, and therefore the oil droplets contract, so that the resin beads to be formed may be unlikely to have a perfectly spherical shape, or a smooth surface may be unlikely to be formed. In addition, when the water-solubility of the organic solvent is too high, the aqueous phase is likely to penetrate partially into the oil droplets, so that solid resin beads may be unlikely to be formed. On the other hand, when the water-solubility of the organic solvent is too low, there is a tendency that the transfer speed of the organic solvent from the oil droplets into the aqueous phase is lowered and a large amount of aqueous phase needs to be used, so that the resin beads may be disadvantageous in terms of production costs. In addition, when the water-solubility of the organic solvent is too low, the organic solvent may be likely to be left in the resin beads. For this reason, the solubility (water-solubility) of the organic solvent to 100 g of water at 25° C. is 0.1 to 50.0 g, preferably 0.5 to 40.0 g, and more preferably 1.0 to 30.0 g.

The liquid amount of the organic solvent contained in the oil phase (first liquid) is preferably 2.0 times or more, and more preferably 2.5 to 15.0 times based on the amount of the cellulose derivative on a mass basis. If the liquid amount of the organic solvent in the oil phase is too small, the cellulose derivative is likely to precipitate rapidly when the organic solvent in the oil droplets transfers into the aqueous phase. For this reason, resin beads to be obtained may be unlikely to have a perfectly spherical shape, or a smooth surface may be unlikely to be formed.

The aqueous phase that is used in the suspension preparation step is a liquid (second liquid) in which a dispersion stabilizer is dissolved in water, such as deionized water. As the dispersion stabilizer, water-soluble polymers, such and water-soluble cellulose, polyvinyl alcohol, and sodium polyacrylate; and inorganic salts, such as hydroxyapatite, tribasic calcium phosphate, and calcium carbonate, can be used. These dispersion stabilizers can be used singly, or two or more of these dispersion stabilizers can be used in combination. Among these dispersion stabilizers, a water-soluble polymer, such as water-soluble cellulose, polyvinyl alcohol, or sodium polyacrylate, is preferably used.

To suppress break or coalescence of the oil droplets in the suspension during transportation, it is preferable that the type and concentration of the dispersion stabilizer which is used in the aqueous phase be set appropriately. The content of the dispersion stabilizer in the aqueous phase is preferably 30% by mass or less, and more preferably 1 to 20% by mass.

It is preferable that the aqueous phase further contain a second organic solvent. The organic solvent (first organic solvent) in the oil phase may transfer rapidly into the aqueous phase depending on the type. Accordingly, by mixing the aqueous phase containing the second organic solvent with the oil phase, the rapid transfer of the first organic solvent in the oil phase into the aqueous phase can be suppressed, so that the resin beads having a higher degree of sphericity and having a further smooth surface can be produced. As the second organic solvent, the same organic solvent as the previously mentioned organic solvent (first organic solvent) which is used in the oil phase, including a preferred first organic solvent, can be used. Note that the first organic solvent and the second organic solvent may be of the same type or of different types.

In the suspension preparation step, the suspension is prepared by mixing the oil phase and the aqueous phase. To mix the oil phase and the aqueous phase, the oil phase may be added to the aqueous phase under stirring, or the aqueous phase may be added to the oil phase under stirring. If necessary, the particle diameters of the oil droplets to be formed are preferably adjusted using an emulsification apparatus, such as a disper or a homogenizer. The particle diameters of the oil droplets to be formed can easily be adjusted by, for example, changing the number of revolutions of the homogenizer to adjust the shear force. As a result, the particle diameters of the resultant resin beads can appropriately be adjusted in such a way as to fall within a desired range.

The liquid amount of the aqueous phase is preferably set to 3.0 times or less, and more preferably 0.2 to 2.8 times based on the liquid amount of the oil phase on a mass basis. By setting the liquid amount of the aqueous phase to the above-described range, the rapid transfer of the organic solvent in the oil droplets into the aqueous phase can be suppressed, so that the resin beads having a higher degree of sphericity and having a further smooth surface can be produced.

The method for producing resin beads of the present invention further includes a step (contraction step) of adding water to the suspension, thereby contracting the oil droplets. By adding water to the suspension, the oil droplets in the suspension can more quickly be contracted. The liquid amount of water to be added to the suspension is preferably 0.5 times or more, and more preferably 1 to 40 times based on the liquid amount of the suspension on a mass basis.

In the contraction step, water is preferably added to the suspension over a certain amount of time. By adding water to the suspension over a certain amount of time, the rapid transfer of the organic solvent in the oil droplets into the aqueous phase can be suppressed, so that the resin beads having a higher degree of sphericity and having a further smooth surface can be produced. Specifically, water is preferably added to the suspension over 30 minutes or longer, water is more preferably added over 45 minutes or longer, and water is particularly preferably added over 60 to 150 minutes.

After the suspension preparation step, unnecessary components, such as the dispersion stabilizer, are removed by, for example, subjecting the produced resin beads to filtration and washing. Subsequently, washing is repeated plural times as necessary, and drying and a cracking treatment are then performed, and thus the objective resin beads can be obtained.

The above-mentioned resin beads are resin particles which have high sphericity (degree of sphericity), which have a smooth surface, which have moist tactile impression, which has favorable stability with time, which is unlikely to generate an offensive smell, and which are obtained by using a natural material as a constituent material. For this reason, when the resin beads are contained, thereby various types of products, such as a cosmetic, a dermatological preparation, a paint, a shaped article, a film, a coating agent, and a resin composition, which are imparted with superior tactile impression, spreadability on the skin, and product stability, can be provided without using resin particles composed of a synthetic material derived from petroleum.

EXAMPLES

Hereinafter, the present invention will specifically be described based on Examples, but the present invention is not limited to these Examples. Note that "part" or "parts," and "%" in Examples and Comparative Examples are each on a mass basis unless otherwise noted.

<Production of Resin Beads>

Example 1

An oil phase was prepared by dissolving 100 parts of cellulose acetate propionate (trade name "CAP-482-0.5," manufactured by Eastman Chemical Company) in 350 parts of ethyl acetate (water-solubility: 8 g/100 g). In addition, an aqueous phase was prepared by dissolving 24 parts of polyvinyl alcohol in 300 parts of ion-exchanged water. The oil phase was added to and mixed with the prepared aqueous phase, and a resultant mixture was stirred using a dissolver at 1,000 rpm for 3 minutes. The mixture was further stirred using the dissolver at 1,800 rpm for 10 minutes to obtain a suspension in which oil droplets were dispersed uniformly. The volume average particle diameter of the oil droplets, measured through observation with an optical microscope and image analysis, was 15 µm.

A dispersion liquid of resin particles (dispersion liquid of resin beads) was obtained by pouring 4,500 parts of ion-exchanged water into the obtained suspension over 75 minutes while the suspension was being stirred using the dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads. FIG. 1 shows an electron micrograph showing a state of surfaces of the obtained resin beads. Further, FIG. 2 shows an electron micrograph showing states of sections of the obtained resin beads.

Example 2

An oil phase was prepared by dissolving 100 parts of cellulose acetate propionate (trade name "CAP-482-0.5," manufactured by Eastman Chemical Company) in 350 parts of ethyl acetate (water-solubility: 8 g/100 g) and 50 parts of methyl acetate (water-solubility: 24.4 g/100 g). In addition, an aqueous phase was prepared by dissolving 42 parts of polyvinyl alcohol in 400 parts of ion-exchanged water. The oil phase was added to and mixed with the prepared aqueous phase, and a resultant mixture was stirred using a dissolver at 1,000 rpm for 3 minutes. The mixture was further stirred using the dissolver at 1,600 rpm for 10 minutes to obtain a suspension in which oil droplets were dispersed uniformly. The volume average particle diameter of the oil droplets, measured through observation with an optical microscope and image analysis, was 18 µm.

A dispersion liquid of resin particles (dispersion liquid of resin beads) was obtained by pouring 5,000 parts of ion-exchanged water into the obtained suspension over 60 minutes while the suspension was being stirred using the dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads.

Example 3

An oil phase was prepared by dissolving 100 parts of cellulose acetate propionate (trade name "CAP-504-0.2," manufactured by Eastman Chemical Company) in 500 parts of ethyl acetate (water-solubility: 8 g/100 g). In addition, an aqueous phase was prepared by dissolving 56 parts of polyvinyl alcohol in 560 parts of ion-exchanged water and then adding 40 parts of ethyl acetate thereto. The oil phase was added to and mixed with the prepared aqueous phase, and a resultant mixture was stirred using a dissolver at 1,000 rpm for 3 minutes. The mixture was further stirred using the dissolver at 1,500 rpm for 10 minutes to obtain a suspension in which oil droplets were dispersed uniformly. The volume average particle diameter of the oil droplets, measured through observation with an optical microscope and image analysis, was 23 µm.

A dispersion liquid of resin particles (dispersion liquid of resin beads) was obtained by pouring 7,000 parts of ion-exchanged water into the obtained suspension over 65 minutes while stirring the suspension was being stirred using the dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads.

Reference Example 4

An oil phase was prepared by dissolving 50 parts of cellulose acetate propionate (trade name "CAP-504-0.2," manufactured by Eastman Chemical Company) and 50 parts of diacetyl cellulose (trade name "CA-398-10," manufactured by Eastman Chemical Company) in 1000 parts of isopropyl acetate (water-solubility: 4 g/100 g). In addition, an aqueous phase was prepared by dissolving 300 parts of polyvinyl alcohol in 2700 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,000 rpm for 10 minutes to obtain a suspension in which oil droplets were dispersed uniformly. The volume average particle diameter of the oil droplets, measured through observation with an optical microscope and image analysis, was 12 µm.

A dispersion liquid of resin particles (dispersion liquid of resin beads) was obtained by pouring 22,000 parts of ion-exchanged water into the obtained suspension over 120 minutes while the suspension was being stirred using the dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads.

Example 5

Resin beads were obtained in the same manner as in Example 1 described previously, except that 100 parts of cellulose acetate propionate was changed to 35 parts of diacetyl cellulose (trade name "CA-398-6," manufactured by Eastman Chemical Company). Resin beads of Example 5 were obtained by mixing 30 parts of the obtained resin beads and 70 parts of the resin beads obtained in Example 3.

Example 6

The resin beads obtained in Example 3 were partially hydrolyzed according to a usual method, and a resultant product was then subjected to filtration, washing, drying, and a cracking treatment to obtain resin beads of Example 6.

Example 7

An oil phase was prepared by dissolving 89 parts of cellulose acetate propionate (trade name "CAP-504-0.2," manufactured by Eastman Chemical Company) in 700 parts of 1-butanol (water-solubility: 8 g/100 g). To the oil phase, 10 parts of fatty acid-treated fine particle titanium oxide (trade name "MT-100TV," manufactured by TAYCA COR- PORATION) and 1 part of a silicone acrylate dispersant (trade name "KP-578," manufactured by Shin-Etsu Chemical Co., Ltd.) were added, and a resultant mixture was mixed/dispersed to prepare an oil phase in which the fine particle titanium oxide was dispersed. In addition, an aqueous phase was prepared by dissolving 50 parts of polyacrylic acid in 850 parts of ion-exchanged water. The oil phase was added to and mixed with the prepared aqueous phase, and a resultant mixture was stirred using a dissolver at 1,000 rpm for 3 minutes. The mixture was further stirred using the dissolver at 2,500 rpm for 20 minutes to obtain a suspension in which oil droplets were dispersed uniformly. The volume average particle diameter of the oil droplets, measured through observation with an optical microscope and image analysis, was 10 μm.

A dispersion liquid of resin particles (dispersion liquid of resin beads) was obtained by pouring 9,000 parts of ion-exchanged water into the obtained suspension over 60 minutes while the suspension was being stirred using the dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads.

Example 8

An oil phase was prepared by dissolving 80 parts of cellulose acetate propionate (trade name "CAP-482-0.5," manufactured by Eastman Chemical Company) in 400 parts of ethyl acetate (water-solubility: 8 g/100 g). To the oil phase, 20 parts of amino acid-treated particle titanium oxide (trade name "NAI-Titanium CR-50," manufactured by Miyoshi Kasei, Inc.) was added, and a resultant mixture was mixed/dispersed to prepare an oil phase in which the titanium oxide was dispersed. In addition, an aqueous phase was prepared by dissolving 32 parts of polyvinyl alcohol in 400 parts of ion-exchanged water. The oil phase was added to and mixed with the prepared aqueous phase, and a resultant mixture was stirred using a dissolver at 1,000 rpm for 3 minutes. The mixture was further stirred using the dissolver at 1,600 rpm for 10 minutes to obtain a suspension in which oil droplets were dispersed uniformly. The volume average particle diameter of the oil droplets, measured through observation with an optical microscope and image analysis, was 14 μm.

A dispersion liquid of resin particles (dispersion liquid of resin beads) was obtained by pouring 8,000 parts of ion-exchanged water into the obtained suspension over 60 minutes while the suspension was being stirred using the dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads.

Comparative Example 1

Cellulose fine particles (trade name "CELLULOBEADS D-5," manufactured by DAITO KASEI KOGYO CO., LTD.) was used as resin beads of Comparative Example 1.

Comparative Example 2

An oil phase was prepared by dissolving 35 parts of diacetyl cellulose (trade name "CA-398-6," manufactured by Eastman Chemical Company) in 350 parts of acetone (water-solubility: ∞ g/100 g). In addition, an aqueous phase was prepared by dissolving 15 parts of polyvinyl alcohol in 300 parts of ion-exchanged water. The oil phase was added to and mixed with the prepared aqueous phase, and a resultant mixture was stirred using a dissolver at 1,000 rpm for 3 minutes. The mixture was further stirred using the dissolver at 1,800 rpm for 10 minutes to obtain a suspension. The volume average particle diameter of the suspension, measured through observation with an optical microscope and image analysis, was 80 μm.

A suspension of resin particles (suspension of resin beads) was obtained by pouring 4,500 parts of ion-exchanged water into the obtained suspension over 45 minutes while the suspension was being stirred using the dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads.

Comparative Example 3

An oil phase was prepared by dissolving 35 parts of diacetyl cellulose (trade name "CA-398-6," manufactured by Eastman Chemical Company) in 350 parts of ethyl acetate (water-solubility: 8 g/100 g). In addition, an aqueous phase was prepared by dissolving 15 parts of polyvinyl alcohol in 300 parts of ion-exchanged water. The oil phase was added to and mixed with the prepared aqueous phase, and a resultant mixture was stirred using a dissolver at 1,000 rpm for 3 minutes. The mixture was further stirred using the dissolver at 1,500 rpm for 10 minutes to obtain a suspension. The volume average particle diameter of the suspension, measured through observation with an optical microscope and image analysis, was 16 μm.

A suspension of resin particles (suspension of resin beads) was obtained by pouring the obtained suspension into 4,500 parts of ion-exchanged water over 10 minutes while the ion-exchanged water was being stirred using a dissolver at 500 rpm. The resin particles were subjected to filtration and washing, and then deflocculated in ion-exchanged water. Further, the resin particles were subjected to filtration and washing, and then dried and subjected to a cracking treatment to obtain resin beads.

Comparative Example 4

An oil phase was prepared by dissolving 35 parts of diacetyl cellulose (trade name "CA-398-6," manufactured by Eastman Chemical Company) in 350 parts of ethyl acetate (water-solubility: 8 g/100 g). In addition, an aqueous phase was prepared by dissolving 15 parts of polyvinyl alcohol in 300 parts of ion-exchanged water. The oil phase was added to and mixed with the prepared aqueous phase, and a resultant mixture was stirred using a dissolver at 1,000 rpm for 3 minutes. The mixture was further stirred using the dissolver at 1,500 rpm for 10 minutes to obtain a suspension. The volume average particle diameter of the suspension, measured through observation with an optical microscope and image analysis, was 16 μm.

A dispersion liquid of resin particles (dispersion liquid of resin beads) was obtained by pouring 4,500 parts of ion-exchanged water into the obtained suspension at once while the suspension was being stirred using the dissolver at 500 rpm. The resin particles were subjected to filtration and washing, and then deflocculated in ion-exchanged water. The obtained resin beads were partially hydrolyzed according to a usual method, and a resultant product was then subjected to filtration, washing, drying, and a cracking treatment to obtain resin beads of Comparative Example 4.

<Evaluation of Resin Beads>

(Volume Average Particle Diameter)

The volume average particle diameter of the resin beads was measured using Coulter Counter (manufactured by Beckman Coulter, Inc.). Results are shown in Table 1.

(Degree of Sphericity)

A SEM image of the resin beads, taken with a scanning electron microscope (SEM), was subjected to image analysis to calculate the degree of circularity C for each resin bead from the following formula (1). Subsequently, the arithmetic average value of the degrees of circularity C for 100 or more resin beads arbitrarily selected was defined as the degree of sphericity. Results are shown in Table 1.

$$C=(4\pi S_1)/(L^2) \quad (1)$$

In the formula (1), $S_1$ represents the area (projected area) of each resin bead in the image, and L represents the length of the outer peripheral part of the resin bead in the image. As the value of the degree of circularity C is closer to 1, each of the shapes of the particles is closer to a perfect sphere.

(Degree of Surface Smoothness)

A SEM image (×5,000) of the resin beads, taken with a scanning electron microscope (SEM), was observed to calculate the degree of smoothness M for each resin bead from the following formula (2). Subsequently, the arithmetic average value of the degrees of smoothness M for 100 or more resin beads arbitrarily selected was defined as the degree of surface smoothness. The results are shown in Table 1. As the value of the degree of smoothness M is closer to 1, the surfaces of the particles are closer to be smooth.

$$M=(1-(S_3)/(S_2))\times100 \quad (2)$$

In the formula (2), $S_2$ represents the area (projected area) of each resin bead in the image, and in the case where a resin bead and a circle that approximates the resin bead are overlapped, $S_3$ represents, in the regions formed by the contour of the resin bead and the contour of the circle, the sum total of the areas of regions that exist inside the contour of the overlapped circle and the area of regions that exist outside the contour of the overlapped circle.

(Degree of Solidity)

A SEM image of sections of the resin beads, taken with a scanning electron microscope (SEM), was subjected to image analysis to calculate the volume of the part filled with the resin for each resin bead. Subsequently, the average value of the volumes of the parts filled with the resin for 20 or more resin beads arbitrarily selected was defined as the degree of solidity (% by volume). Results are shown in Table 1.

(Acethyl Group Content Ratio and Propionyl Group Content Ratio)

The acetyl group content ratio in the resin beads and the propionyl group content ratio in the resin beads were measured and calculated according to the contents described in Japanese Patent Application Publication No. 2006-523752 (mainly, the contents described in paragraphs [0136] to [0145]). Results are shown in Table 1.

(Tactile Impression)

Sensory evaluation on the tactile impression of the resin beads by a panel test of ten people was performed. The "slickness," the "spreadability on the skin," and the "moist feeling" were totally decided when the resin beads were touched, and the tactile impression of the resin beads was graded on a scale of 1 to 5 according to the evaluation criteria described below to calculate the average mark in ten people. Results are shown in Table 1.

5: Excellent
4: Above average
3: Average
2: Below average
1: Poor (Odor (Product Stability))

Sensory evaluation on the odor of the resin beads by a panel test of five people was performed. Into a 30 mL volume sealable glass bottle, 4.0 g of the resin beads, and pure water in an amount such that the water content of the resin beads was 10% were placed, and the glass bottle was sealed to perform an acceleration test of 7 days in a thermostatic chamber of 70° C. After the glass bottle was cooled to room temperature, the lid was opened to check a change in the odor. The odor of the resin beads after the acceleration test was compared with the odor of the resin beads before the acceleration test which was defined as the reference odor, and the odor of the resin beads after the acceleration test was graded on a scale of 1 to 5 according to the evaluation criteria described below to calculate the average mark in five people. Results are shown in Table 1.

5: A change is not felt.
4: A change is somewhat felt.
3: A change is felt.
2: A somewhat strong change is felt.
1: A strong change is felt.

TABLE 1

|  | Volume average particle diameter (μm) | Degree of sphericity | Degree of surface smoothness (%) | Degree of solidity (vol %) | Content ratio of acetyl group (%) | Content ratio of propionyl group (%) | Tactile impression | Odor |
|---|---|---|---|---|---|---|---|---|
| Example 1 | 10 | 0.96 | 97 | 95 | 1.5 | 45.0 | 4.5 | 4.8 |
| Example 2 | 12 | 0.95 | 96 | 75 | 1.5 | 45.0 | 4.6 | 4.7 |
| Example 3 | 15 | 0.99 | 100 | 99 | 0.5 | 42.5 | 4.8 | 4.7 |
| Reference Example 4 | 6 | 0.95 | 96 | 85 | 20.2 | 21.3 | 4.3 | 4.2 |
| Example 5 | 14 | 0.98 | 97 | 97 | 12.4 | 31.5 | 4.5 | 4.5 |
| Example 6 | 14 | 0.98 | 97 | 97 | 0.0 | 14.0 | 4.5 | 4.5 |
| Example 7 | 4 | 0.95 | 91 | 95 | 0.4 | 37.8 | 4.2 | 4.6 |
| Example 8 | 14 | 0.89 | 88 | 95 | 0.4 | 36.0 | 4.3 | 4.5 |
| Comparative Example 1 | 13 | 0.67 | 62 | 66 | 0.0 | 0.0 | 2.1 | 4.1 |
| Comparative Example 2 | 80 | 0.42 | 40 | 36 | 39.8 | 0.0 | 1.2 | 1.3 |

TABLE 1-continued

|  | Volume average particle diameter (μm) | Degree of sphericity | Degree of surface smoothness (%) | Degree of solidity (vol %) | Content ratio of acetyl group (%) | Content ratio of propionyl group (%) | Tactile impression | Odor |
|---|---|---|---|---|---|---|---|---|
| Comparative Example 3 | 16 | 0.55 | 51 | 48 | 39.8 | 0.0 | 2.1 | 1.3 |
| Comparative Example 4 | 16 | 0.64 | 65 | 63 | 28.0 | 0.0 | 2.3 | 2.6 |

<Production of Cosmetic>

(Cosmetic-1)

A cosmetic-1 was produced by mixing components which had conventionally been used as raw materials for cosmetics. Specifically, each of silicone-treated powders (mica, talc, fine particle titanium oxide, and barium sulfate) and the resin beads were first blended according to the blending amounts shown in Table 2, and a resultant mixture was mixed until it became uniform to obtain a powder mixture. Subsequently, a mixture (additional components) obtained by mixing Vaseline, squalane, and glyceryl trioctanoate was added to the powder mixture, and a resultant mixture was mixed until it became uniform. Thereafter, the mixture was filled in a container, and press shaping was performed as necessary to obtain the cosmetic-1.

TABLE 2

|  | Component name | Blending amount (parts) |
|---|---|---|
| Additional components | Vaseline | 2.5 |
|  | Squalane | 2.5 |
|  | Glyceryl trioctanoate | 2.5 |
| Powder mixture | Silicone-treated mica | 40.0 |
|  | Silicone-treated talc | 33.0 |
|  | Silicone-treated fine particle titanium oxide | 5.0 |
|  | Silicone-treated barium sulfate | 10.0 |
|  | Resin beads | 4.5 |

(Cosmetic-2)

A cosmetic-2, which is a Sun-Cut milky lotion, was produced by mixing components which had conventionally been used as raw materials for cosmetics. Specifically, silicone oil, an ultraviolet protective agent, an emulsifier, a dispersant, isotridecyl isononanoate, and the resin beads were first blended according to the blending amounts shown in Table 3 and mixed to prepare oil phase components. Further, purified water, dipropylene glycol, sodium chloride, and sodium citrate were blended according to the blending amounts shown in Table 3 and mixed to prepare aqueous phase components. Subsequently, the aqueous phase components were added to the prepared oil phase components while the oil phase components were being stirred, and thus emulsification was performed to obtain the cosmetic-2.

TABLE 3

|  | Component name | Blending amount (parts) |
|---|---|---|
| Aqueous phase components | Purified water | 16.3 |
|  | Dipropylene glycol | 2.5 |
|  | Sodium chloride | 1.0 |
|  | Sodium citrate | 0.2 |

TABLE 3-continued

|  | Component name | Blending amount (parts) |
|---|---|---|
| Oil phase components | Silicone oil | 30.0 |
|  | Ultra violet protective agent | 35.0 |
|  | Emulsifier | 5.0 |
|  | Dispersant | 1.0 |
|  | Isotridecyl isononanoate | 4.0 |
|  | Resin beads | 5.0 |

<Evaluation of Cosmetic-1>

(Tactile Impression and Spreadability on Skin)

Sensory evaluation on the tactile impression and the spreadability on the skin of the cosmetic-1 by a panel test of ten people was performed. The "goodness of the tactile impression" and the "spreadability on the skin" were decided and graded on a scale of 1 to 5 according to the evaluation criteria described below to calculate the average mark in ten people. Results are shown in Table 4.

5: Excellent

4: Above average

3: Average

2: Below average

1: Poor (Odor (Product Stability))

Sensory evaluation on the odor of the cosmetic-1 by a panel test of five people was performed. Into a 30 mL volume sealable glass bottle, 4.0 g of the cosmetic-1 (powder) was placed, and the glass bottle was sealed to perform an acceleration test of 7 days in a thermostatic chamber of 70° C. After the glass bottle was cooled to room temperature, the lid was opened to check a change in the odor. The odor of the powder after the acceleration test was compared with the odor of the powder before the acceleration test which was defined as the reference odor, and the odor of the powder after the acceleration test was graded on a scale of 1 to 5 according to the evaluation criteria described below to calculate the average mark in five people. Results are shown in Table 4.

5: A change is not felt.

4: A change is somewhat felt.

3: A change is felt.

2: A somewhat strong change is felt.

1: A strong change is felt.

TABLE 4

| Cosmetic-1 | Resin beads | Tactile impression | Spreadability on skin | Odor |
|---|---|---|---|---|
| Example A1 | Example 1 | 4.8 | 4.6 | 4.8 |
| Example A2 | Example 2 | 4.8 | 4.7 | 4.7 |
| Example A3 | Example 3 | 4.8 | 4.8 | 4.7 |
| Reference Example A4 | Reference Example 4 | 4.6 | 4.4 | 4.6 |
| Example A5 | Example 5 | 4.9 | 4.8 | 4.5 |
| Example A6 | Example 6 | 4.3 | 4.3 | 4.6 |
| Example A7 | Example 7 | 4.7 | 4.8 | 4.5 |
| Example A8 | Example 8 | 4.7 | 4.8 | 4.5 |
| Comparative Example A1 | Comparative Example 1 | 1.9 | 2.1 | 4.3 |
| Comparative Example A2 | Comparative Example 2 | 1.1 | 1.1 | 1.3 |
| Comparative Example A3 | Comparative Example 3 | 1.9 | 2.1 | 1.4 |
| Comparative Example A4 | Comparative Example 4 | 1.8 | 2.3 | 2.4 |

<Evaluation of Cosmetic-2>
(Tactile Impression, Spreadability on the Skin, and Transparency)

Sensory evaluation on the tactile impression, the spreadability on the skin, and the transparency of the cosmetic-2 by a panel test of ten people was performed. The "goodness of the tactile impression," the "spreadability on the skin," and the "transparency" were decided and graded on a scale of 1 to 5 according to the evaluation criteria described below to calculate the average mark in ten people. Results are shown in Table 5.

5: Excellent
4: Above average
3: Average
2: Below average
1: Poor (Odor (Product Stability))

Sensory evaluation on the odor of the cosmetic-2 by a panel test of five people was performed. Into a 30 mL volume sealable glass bottle, 4.0 g of the cosmetic-2 (liquid) was placed, and the glass bottle was sealed to perform an acceleration test of 7 days in a thermostatic chamber of 70° C. After the glass bottle was cooled to room temperature, the lid was opened to check a change in the odor. The odor of the liquid after the acceleration test was compared with the odor of the liquid before the acceleration test which was defined as the reference odor, and the odor of the liquid after the acceleration test was graded on a scale of 1 to 5 according to the evaluation criteria described below to calculate the average mark in five people. Results are shown in Table 5.

5: A change is not felt.
4: A change is somewhat felt.
3: A change is felt.
2: A somewhat strong change is felt.
1: A strong change is felt.

TABLE 5

| Cosmetic-2 | Resin beads | Tactile impression | Spreadability on skin | Transparency | Odor |
|---|---|---|---|---|---|
| Example B1 | Example 1 | 4.6 | 4.7 | 4.7 | 4.7 |
| Example B2 | Example 2 | 4.7 | 4.8 | 4.8 | 4.6 |
| Example B3 | Example 3 | 4.8 | 4.8 | 4.8 | 4.5 |
| Reference Example B4 | Reference Example 4 | 4.4 | 4.5 | 4.5 | 4.6 |
| Example B5 | Example 5 | 4.9 | 4.8 | 4.8 | 4.6 |
| Example B6 | Example 6 | 4.3 | 4.4 | 4.1 | 4.6 |
| Example B7 | Example 7 | 4.3 | 4.4 | 4.1 | 4.6 |
| Comparative Example B1 | Comparative Example 1 | 2.1 | 1.6 | 2.8 | 4.4 |
| Comparative Example B2 | Comparative Example 2 | 1.1 | 1.1 | 1.5 | 1.9 |
| Comparative Example B3 | Comparative Example 3 | 2.1 | 1.7 | 2.8 | 2.1 |
| Comparative Example B4 | Comparative Example 4 | 2.2 | 2.2 | 2.7 | 2.6 |

As shown in Tables 4 and 5, it is understood that cosmetics having superior tactile impression, spreadability on the skin, transparency, and product stability were able to be produced by using the resin beads of Examples. Further, it was ascertained that properties such as superior tactile impression, transparency, spreadability, and product stability were also able to be imparted not only to a cosmetic but also to various types of products, such as a dermatological preparation, a paint, a shaped article, a film, a coating agent, and a resin composition, by using the resin beads of Examples.

INDUSTRIAL APPLICABILITY

The resin beads of the present invention have properties equal to or superior to those of the resin beads formed with a synthetic material derived from petroleum. For this reason, when the resin beads of the present invention are used, thereby products, such as cosmetics, exhibiting satisfactory tactile impression, having favorable spreadability on the skin, having transparency, and having stable product quality can be provided without using resin beads formed with a synthetic material derived from petroleum. Accordingly, the resin beads of the present invention are useful as a constituent material for various types of products, such as, for example, a cosmetic, a dermatological preparation, a paint, a shaped article, a film, a coating agent, and a resin composition.

The invention claimed is:

1. Resin beads formed with a resin comprising a cellulose derivative as a main component, wherein
the cellulose derivative is at least one material selected from the group consisting of cellulose acetate, cellulose acetate propionate, ethyl cellulose, and hydroxypropyl methyl cellulose,
the resin beads have:
a volume average particle diameter of 50 μm or smaller,
a degree of sphericity in a range from 0.7 to 1.0,
a degree of surface smoothness in a range from 80 to 100%,
an amount of an acetyl group in the resin beads in a range of 1.5% by mass or less, and
an amount of a propionyl group in the resin beads in a range of 10% by mass or more.

2. The resin beads according to claim 1, wherein the cellulose derivative is cellulose acetate propionate.

3. The resin beads according to claim 1, having a degree of solidity in a range from 70 to 100% by volume.

4. The resin beads according to claim 1, wherein the resin beads comprise at least one material selected from the group consisting of a pigment and a dye.

5. The resin beads according to claim 1, wherein the resin beads comprise: a pigment; and at least one material selected from the group consisting of a surfactant, a dispersant, and a polymer dispersant.

6. The resin beads according to claim 4, wherein the pigment is a treated pigment treated with at least one material selected from the group consisting of silicone, a fatty acid, a metal salt of a fatty acid, an amino acid, and a metal salt of an amino acid.

7. The resin beads according to claim 1, wherein the resin beads comprise at least one agent selected from the group consisting of an ultraviolet absorbing agent and an ultraviolet scattering agent.

8. The resin beads according to claim 1, wherein the resin beads are treated beads treated with at least one material selected from the group consisting of silicone, a fatty acid, a metal salt of a fatty acid, an amino acid, and a metal salt of an amino acid.

9. A method for producing resin beads, being a method for producing the resin beads according to claim 1, the method comprising:
mixing an oil phase comprising the cellulose derivative and an organic solvent that dissolves the cellulose derivative and has a solubility to 100 g of water at 25° C. in a range from 0.1 to 50.0 g with an aqueous phase comprising a dispersion stabilizer, thereby preparing a suspension comprising oil droplets that comprises the cellulose derivative and the organic solvent; and
adding water to the suspension, thereby contracting the oil droplets.

10. The method for producing resin beads according to claim 9, wherein the water is added to the suspension over a course of 30 minutes or longer.

11. The method for producing resin beads according to claim 9, wherein a liquid amount of the water to be added to the suspension is 0.5 times or more based on a liquid amount of the suspension on a mass basis.

12. The method for producing resin beads according to claim 9, wherein the aqueous phase further comprises a second organic solvent.

13. The method for producing resin beads according to claim 9, wherein a liquid amount of the aqueous phase is 3.0 times or less based on a liquid amount of the oil phase on a mass basis.

14. The method for producing resin beads according to claim 9, wherein the organic solvent is at least one material selected from the group consisting of a ketone-based solvent, an ester-based solvent, an alcohol, a glycol, an ether-based solvent, a halogenated alkyl, and a nitrated alkyl.

15. The method for producing resin beads according to claim 9, wherein a liquid amount of the organic solvent is 2.0 times or more based on an amount of the cellulose derivative on a mass basis.

16. The method for producing resin beads according to claim 9, wherein the dispersion stabilizer is a water-soluble polymer.

17. The method for producing resin beads according to claim 9, wherein a content of the dispersion stabilizer in the aqueous phase is in a range of 30% by mass or less.

18. A product that is a cosmetic, a dermatological preparation, a paint, a shaped article, a film, a coating agent, or a resin composition, the product comprising resin beads, wherein
the resin beads are the resin beads according to claim 1.

* * * * *